United States Patent [19]

Leining

[11] Patent Number: 5,534,090
[45] Date of Patent: Jul. 9, 1996

[54] DOSIMETER CAPSULE INDICATING SERVICE LIFE OF A ROCKET MOTOR

[75] Inventor: Richard B. Leining, Salt Lake City, Utah

[73] Assignee: The United States of America as represented by the Secretary of the Air Force, Washington, D.C.

[21] Appl. No.: 684,417

[22] Filed: Dec. 20, 1984

[51] Int. Cl.⁶ .................................................. G01N 21/01
[52] U.S. Cl. ....................... 149/15; 149/14; 73/116; 116/220; 116/70; 102/347; 422/58; 60/253
[58] Field of Search ................... 73/23, 35, 116; 116/216, 220, DIG. 8, 70; 422/55, 58; 149/14, 15; 102/347; 60/253

[56] References Cited

U.S. PATENT DOCUMENTS

| | | | |
|---|---|---|---|
| 1,466,117 | 8/1923 | Chaney | 116/216 |
| 2,460,215 | 1/1949 | Chase | 99/192 |
| 3,217,689 | 11/1965 | Knight et al. | 116/114 |
| 3,996,007 | 12/1976 | Fang et al. | 116/114 |
| 4,040,805 | 8/1977 | Nelms et al. | 73/23 |
| 4,143,617 | 3/1979 | Youngren | 73/35 |
| 4,382,700 | 5/1983 | Youngren | 116/216 |

Primary Examiner—Charles T. Jordan
Assistant Examiner—Daniel Jenkins
Attorney, Agent, or Firm—Bobby D. Scearce; Thomas L. Kundert

[57] ABSTRACT

A novel dosimeter capsule for indicating the condition of the solid propellant contained within a rocket motor to provide a measure of the remaining service life of the motor is described, which comprises a sealed expandable container and a portion of the solid propellant sealed therein and sized to fill the available volume within the container, the propellant portion containing a smaller concentration of chemical stabilizer than that which characterizes the solid propellant contained in the rocket motor, so that the propellant portion will deteriorate at a predictably faster rate than the rocket motor propellant, resulting in an increase of pressure within the expandable container of evolved gaseous products of the decomposition of the propellant portion and an accompanying bulge or protrusion of the container from its receptacle on the rocket motor casing corresponding to the increased internal pressure. The capsule of the invention may be applicable to many chemically stabilized solid propellants, especially those containing nitrate esters, such as double-base propellants whether extruded, powder-cast, composite-modified, plastisol, or cross-linked.

6 Claims, 1 Drawing Sheet

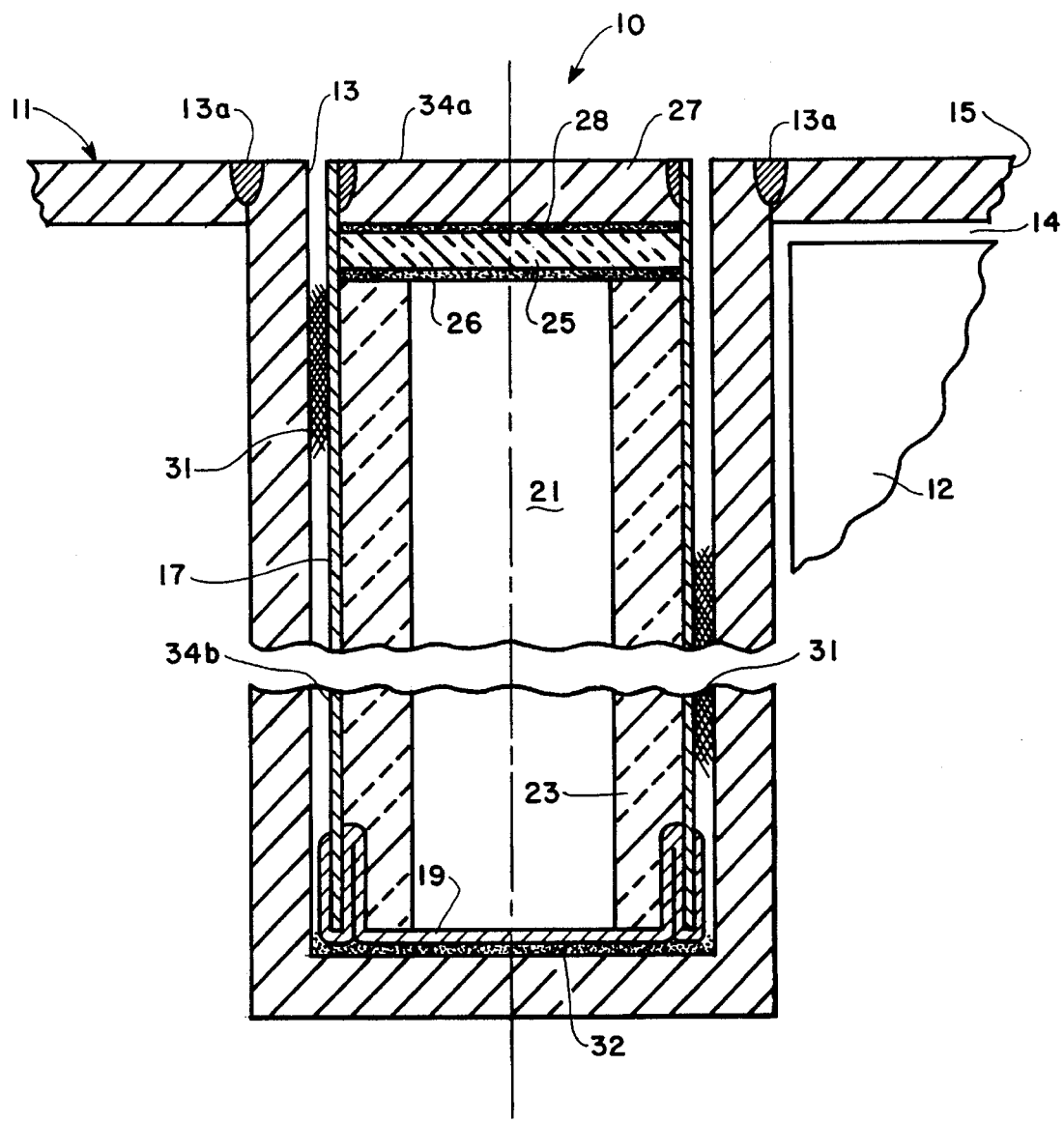

DOSIMETER CAPSULE INDICATING SERVICE LIFE OF A ROCKET MOTOR

RIGHTS OF THE GOVERNMENT

The invention described herein may be manufactured and used by or for the Government of the United States for all governmental purposes without the payment of any royalty.

BACKGROUND OF THE INVENTION

The present invention relates to a novel indicator for gauging the condition of solid propellant within a rocket motor and providing a visible display indicative of the approach of the end of the service life of the motor.

In a solid propellant rocket engine, the propellant is contained within the combustion chamber of the engine in solid form. The physical mass or body of the propellant, referred to as the grain, may take on a variety of configurations defining an internal surface geometry to aid in even, controlled burning of the propellant in the operation of the rocket engine. The solid propellant normally contains all the constituents necessary for sustaining fuel combustion to provide thrust, and conventionally comprises a mixture of constituents including an oxidizer such as a nitrate or perchlorate, a fuel matrix such as an organic resin, plastic, or rubber, and additives, stabilizers, and inhibitors to facilitate propellant grain fabrication, to control grain burning rate, to preserve physical and chemical stability, and to retard propellant grain deterioration in storage. By reason of their chemical composition and physical configuration, solid propellant grains may be stored for considerable periods of time and made available for use without substantial preparation as compared to other rocket engine propellant types, such as those comprising liquid cryogens.

Most solid propellants are sensitive to variations in ambient temperature and humidity, the grains having a tendency to soften on hot days and embrittle on cold days. It may therefore be necessary to restrict the ambient temperature range over which the rocket is deemed operable, depending on the particular propellant composition, and to monitor and control the temperature and moisture conditions under which the fueled rocket, or the propellant grain material separately, should be stored, particularly for rocket engines required to be maintained in a state of operational readiness for substantial periods of time. However, practical limits exist as to the frequency and thoroughness of inspection and the degree of environmental protection which can be accorded rocket motors within tactical weapons deployed in the field. Further, life cycles of individual air-launched missiles powered by the rocket motors may vary according to environmental conditions encountered on multiple flights on which the missiles are carried.

The present invention provides a reliable visual dosimeter for use with a solid propellant rocket motor to indicate the shelf life or, more accurately, the approach of the end of the service life of a solid propellant fueled rocket motor. The capsule of the present invention comprises an expandable metal container including a sample of the propellant used in the rocket motor, but with a slightly smaller concentration of chemical stabilizer than that included in the rocket motor propellant composition. The capsule is disposed at a suitable location within the casing of the rocket near the motor so that the capsule is exposed to substantially similar thermal and other environmental conditions as that to which the propellant of the motor is exposed. By reason of the somewhat lower concentration of chemical stabilizer in the sample, the sample decomposes at a predictably faster rate than the rocket motor propellant composition. Gaseous products of the decomposition of the sample expand the metal container of the dosimeter capsule, which in an expanded condition is conspicuous by its color and protrusion, thereby providing by analogy an indication of the condition of the solid propellant in the rocket motor. The capsule therefore may provide an effective measure of the approach of the end of the service life of the rocket motor. Substantial improvement in operational reliability of solid propellant rocket engines may therefore be provided through use of the invention described herein.

It is, therefore, a principal object of the present invention to provide a dosimeter for indicating the condition of the solid propellant of a rocket motor.

It is a further object of the invention to provide a dosimeter capsule disposable within the casing of a rocket or the like for indicating the approach of the end of the service life of a solid propellant rocket motor.

It is yet a further object of the invention to provide a dosimeter capsule for providing a quick, thorough and reliable indication of the condition of a solid propellant rocket motor in storage.

These and other objects of the present invention will become apparent as the detailed description of certain representative embodiments thereof proceeds.

SUMMARY OF THE INVENTION

In accordance with the foregoing principles and objects of the present invention, a novel dosimeter capsule for indicating the condition of the solid propellant contained within a rocket motor to provide a measure of the remaining service life of the motor is described, which comprises a sealed expandable container and a portion of the solid propellant sealed therein and sized to fill the available volume within the container, the propellant portion containing a smaller concentration of chemical stabilizer than that which characterizes the solid propellant contained in the rocket motor, so that the propellant portion will deteriorate at a predictably faster rate than the rocket motor propellant, resulting in an increase of pressure within the expandable container of evolved gaseous products of the decomposition of the propellant portion and an accompanying bulge or protrusion of the container from its receptacle on the rocket motor casing corresponding to the increased internal pressure. The capsule of the invention may be applicable to many chemically stabilized solid propellants, especially those containing nitrate esters, such as double-base propellants whether extruded, powder-cast, composite-modified, plastisol, or cross-linked.

DESCRIPTION OF THE DRAWINGS

The present invention will be more clearly understood from the following detailed description of certain representative embodiments thereof read in conjunction with the accompanying drawing which is a view in axial section of a representative capsule according to the invention as disposed within a recess in the casing of a rocket.

DETAILED DESCRIPTION

Referring now to the accompanying drawing, shown therein is an axial sectional view of a representative embodiment of the novel dosimeter capsule 10 of the present invention, as it may be disposed within the casing of a rocket 11 or the like. In a solid propellant rocket motor, the propellant grain comprises a mixture of all the constituents necessary for combustion to provide thrust. Accordingly, the propellant may comprise an oxidizer such as ammonium or potassium perchlorate, ammonium or potassium nitrate, or any of various organic nitrates, such as nitroglycerine (NG), butane triol trinitrate (BTTN), trimethylol ethane trinitrate (TMETN), or triethylene glycol dinitrate (TEGDN), in an organic fuel matrix, such as synthetic rubber, synthetic resin, cellulose or its derivatives including cellulose nitrate, or a polyester, polyether, polycaprolactone, or the like. A chemical stabilizer such as methyl nitro aniline (MNA), 4-nitro diphenyl amine (4-NDPA), 2-nitro diphenyl amine (2-NDPA), resorcinol, or the like may be included in order to retard deterioration of the propellant grain that may occur in long term storage. If TEGDN or TMETN is substituted for NG or BTTN, less stabilizer may be required. In the representative embodiment of the invention described herein and illustrated in the drawing, capsule 10 was configured to indicate the expiration of the service life of an air-launched tactical missile including a rocket motor 11 assumed to comprise a solid propellant 12 containing a nitrate ester and including about one weight percent methyl nitro aniline (MNA) chemical stabilizer. It is noted, however, that the teachings herein are not limited in applicability to the named propellant and stabilizer, since the principles of the invention as may be applied to other propellants and chemical stabilizers as might occur to one with skill in the art upon a reading hereof. Accordingly, in a rocket 11 having a solid propellant 12, a well or recess 13 may be provided in motor casing 15 in order to receive the dosimeter capsule 10 of the present invention. Capsule may comprise a cylinder about one inch in diameter by about two inches in overall length, and recess 13 may be sized accordingly, although size of capsule 10 is not limiting of the invention herein. Recess 13 (and capsule 10) should have diameter large enough to expose sufficient surface area of capsule 10 both at the surface of casing 15 and at the interface with recess 13 to be representative of the environment to which solid propellant 12 is exposed (such as in storage of rocket 11), and will have sufficient axial length in order to simulate accurately heat transfer and other factors affecting rocket propellant 12 as bonded with adhesive 14 to motor casting 15. Recess 13 may be defined by walls comprising the same material of which casing 15 is comprised and may be welded, brazed, silver soldered rolled, or otherwise conventionally secured within casing 15 such as represented by annular joint 13a.

Capsule 10 comprises an expandable container, bellows, or the like, such as represented by metal tube 17 sized to fit snugly within recess 13 with an expandable metal cap 19 press fit or bonded gas-tight to the inner end thereof. Tube 17 contains a sample 21 of the propellant used within motor 12 of rocket 11, the composition of which is modified slightly in order to provide the desired characteristics for capsule 10. Propellant sample 21 may occupy substantially the entire internal volume of tube 17, or as illustrated in the drawing, a cylindrical tube of insulation 23 which is inert or otherwise compatible or nonreactive with propellant sample 21 may be disposed around sample 21 within tube 17 in order to insulate sample 21 from exposure to widely and rapidly fluctuating temperature excursions not affecting propellant 12 to which the surface of tube 17 may be exposed. In order to closely simulate the thermal environment to which the rocket propellant of motor 12 is exposed, a layer 25 of insulation substantially identical in composition and thickness to that which may surround propellant 12 may be inserted as illustrated and affixed to the outer end of propellant sample 21 (and insulative tube 23 if included) with an adhesive layer 26. Adhesive layer 26 has the same composition and thickness as case-bonding adhesive layer 14 so as to duplicate any chemical reactions at the case bond of propellant 12. A lid 27 is provided for tube 17 as illustrated, of material and thickness like motor case 15, and may be secured to insulation layer 25 by a layer of adhesive 28. Adhesive layer 28 is preferably characterized by resistance to decomposition at the temperatures which capsule 10 will experience, and may include epoxy resin, curative, optional inert filler such as silica, or the like. Lid 27 may be otherwise conventionally secured to tube 17 by welding, brazing, soldering, rolling, swaging, or the like.

In order to optimize thermal conduction to and from capsule 10 as installed within recess 13, and thereby to subject capsule 10 as closely as practicable to the identical (possibly variable) environment to which the propellant within motor 12 is subjected, capsule 10 is sized to snugly fit within recess 13. Accordingly, a thermally conducting lubricant 31, such as silicone grease, graphite powder, or molybdenum sulfide may be applied to the outer surface of capsule 10. Capsule 10 may otherwise be secured within recess 13 by an adhesive layer 32 of the type and character described above for adhesive layer 28. The outer surface of tube 17 and of lid 27 may be provided with coats of paint 34a,b in order to retard corrosion, present an end surface of substantially identical visual and radiant heat absorbing character as that of the remainder of casing 15. Coating 34b makes the eventual protrusion of tube 17 conspicuous against the background of casing 15. Coating 34bis preferably red in color.

As a general proposition, data on the rates of depleting a chemical stabilizer and of generating gas therefrom are well known for bulk propellants. The data show that gas evolution accelerates when the stabilizer is depleted. Capsule 10 is therefore configured to contain the same propellant 12 as motor 11, but with somewhat less chemical stabilizer concentration (about four-fifths as much MNA). The expandable container (tube 17, cap 19) is therefore constructed to be impervious to the least-soluble gaseous products of the decomposition of the nitrate ester, principally nitrogen and nitrous oxide, contained in the solid propellant. Capsule 10 is further configured to have negligible free volume with sample 21 inserted whereby the evolved gas expands metal tube 17 upon absorption of sufficient thermal energy, such that capsule 10 is conspicuous by its expansion and exposure of color 34b as compared to adjacent areas of casing 15.

The present invention, as hereinabove described, therefore provides a novel dosimeter capsule for indicating the remaining service life of a tactical rocket motor by monitoring the condition of a sample of the rocket motor propellant. It is understood that certain modifications to the invention as described may be made, as might occur to one with skill in the field of this invention, within the scope of the appended claims. Therefore, all embodiments contemplated hereunder which achieve the objectives of the invention have not been shown in complete detail. Other embodiments may be developed without departing from the spirit of this invention or from the scope of the appended claims.

I claim:

1. A dosimeter capsule for indicating the condition of solid propellant including a chemical stabilizer, such as contained within a rocket motor or the like, comprising:

a. a sealed expandable container; and b. a portion of said solid propellant sealed within said expandable container, said portion containing a smaller concentration of chemical stabilizer than that which characterizes the said solid propellant contained within said rocket motor, said portion sized to substantially fill the available volume of said expandable container.

2. The capsule as recited in claim 1 further comprising a layer of inert insulation surrounding said portion within said container.

3. The capsule as recited in claim 1 wherein said portion comprises a solid propellant selected from the group containing nitrate ester consisting of nitroglycerine, butane triol trinitrate, trimethylol ethane trinitrate, triethylene glycol dinitrate and cellulose nitrate, and a chemical stabilizer selected from a group consisting of methyl nitro aniline, 4-nitro diphenyl amine, 2-nitro diphenyl amine, and resorcinol.

4. In a rocket motor containing a solid propellant including a chemical stabilizer, said motor including means for indicating the condition of said propellant, an improvement wherein said indicating means comprises:

a. a sealed expandable container disposed adjacent said motor; and b. a portion of said solid propellant sealed within said expandable container, said portion containing a smaller concentration of chemical stabilizer than that which characterizes said solid propellant contained within said rocket motor, said portion sized to substantially fill the available volume of said expandable container.

5. The motor as recited in claim 4 further comprising a layer of inert insulation surrounding said portion within said container.

6. The motor as recited in claim 4 wherein said portion comprises a solid propellant selected from the group containing nitrate ester consisting of nitrogylcerine, butane triol trinitrate, trimethylol ethane trinitrate, triethylene glycol dinitrate and cellulose nitrate, and a chemical stabilizer selected from a group consisting of methyl nitro aniline, 4-nitro diphenyl amine, 2-nitro diphenyl amine, and resorcinol.

* * * * *